United States Patent
Feitisch et al.

(10) Patent No.: US 9,618,391 B2
(45) Date of Patent: Apr. 11, 2017

(54) COLLISIONAL BROADENING COMPENSATION USING REAL OR NEAR-REAL TIME VALIDATION IN SPECTROSCOPIC ANALYZERS

(71) Applicant: Spectrasensors, Inc., Rancho Cucamonga, CA (US)

(72) Inventors: Alfred Feitisch, Los Gatos, CA (US); Xiang Liu, Rancho Cucamonga, CA (US); Hsu-Hung Huang, Rancho Cucamonga, CA (US); Wenhai Ji, Fontana, CA (US); Richard L. Cline, Rancho Cucamonga, CA (US)

(73) Assignee: SpectraSensors, Inc., Rancho Cucamonga, CA (US)

( * ) Notice: Subject to any disclaimer, the term of this patent is extended or adjusted under 35 U.S.C. 154(b) by 0 days.

(21) Appl. No.: 14/634,364

(22) Filed: Feb. 27, 2015

(65) Prior Publication Data
US 2016/0011047 A1 Jan. 14, 2016

Related U.S. Application Data

(63) Continuation of application No. 13/428,591, filed on Mar. 23, 2012, now Pat. No. 8,976,358.

(51) Int. Cl.
*G01J 3/02* (2006.01)
*G01N 21/3504* (2014.01)
(Continued)

(52) U.S. Cl.
CPC .............. *G01J 3/0297* (2013.01); *G01J 3/42* (2013.01); *G01N 21/05* (2013.01); *G01N 21/274* (2013.01);
(Continued)

(58) Field of Classification Search
None
See application file for complete search history.

(56) References Cited

U.S. PATENT DOCUMENTS 4,110,619 A 8/1978 Zorner
4,803,370 A 2/1989 Eckles
(Continued)

OTHER PUBLICATIONS

"In-Situ Sensors for the Chemical Industry—Final Report," the Dow Chemical Company, Principle investigator: Dr. J.D. Tate, project No. DE-FC36-o21D14428, pp. 1-37, Jun. 30, 2006.
(Continued)

*Primary Examiner* — Kara E Geisel
*Assistant Examiner* — Shawn Decenzo
(74) *Attorney, Agent, or Firm* — Mintz Levin Cohn Ferris Glovsky and Popeo, P.C.

(57) ABSTRACT

Validation verification data quantifying an intensity of light reaching a detector of a spectrometer from a light source of the spectrometer after the light passes through a validation gas across a known path length can be collected or received. The validation gas can include an amount of an analyte compound and an undisturbed background composition that is representative of a sample gas background composition of a sample gas to be analyzed using a spectrometer. The sample gas background composition can include one or more background components. The validation verification data can be compared with stored calibration data for the spectrometer to calculate a concentration adjustment factor, and sample measurement data collected with the spectrometer can be modified using this adjustment factor to compensate for collisional broadening of a spectral peak of the analyte compound by the background components. Related methods, articles of manufacture, systems, and the like are described.

20 Claims, 4 Drawing Sheets

(51) Int. Cl.
    *G01N 21/05*     (2006.01)
    *G01N 21/27*     (2006.01)
    *G01J 3/42*     (2006.01)
    *G01N 21/39*     (2006.01)
    *G01N 21/03*     (2006.01)

(52) U.S. Cl.
    CPC ......... *G01N 21/3504* (2013.01); *G01N 21/39* (2013.01); *G01N 2021/0314* (2013.01); *G01N 2021/399* (2013.01); *G01N 2201/127* (2013.01); *G01N 2201/1211* (2013.01); *G01N 2201/1218* (2013.01)

(56) References Cited

U.S. PATENT DOCUMENTS

| | | |
|---|---|---|
| 4,849,636 A | 7/1989 | Fertig, Sr. |
| 5,457,320 A * | 10/1995 | Eckles ............... G01N 21/3504 250/343 |
| 5,900,635 A | 5/1999 | Weckstrom |
| 6,147,351 A | 11/2000 | Huiku |
| 6,527,398 B1 | 3/2003 | Fetzer |
| 6,844,554 B2 | 1/2005 | Karlsson |
| 7,508,521 B2 | 3/2009 | Liu et al. |
| 7,704,301 B2 | 4/2010 | Zhou et al. |
| 7,819,946 B2 | 10/2010 | Zhou et al. |
| 8,152,900 B2 | 4/2012 | Zhou et al. |
| 8,178,832 B1 | 5/2012 | Wong |
| 8,358,417 B2 | 1/2013 | Feitisch et al. |
| 8,953,165 B2 | 2/2015 | Feitisch et al. |
| 8,976,358 B2 | 3/2015 | Feitisch et al. |
| 2010/0201989 A1 | 8/2010 | Zhou et al. |
| 2011/0093215 A1 | 4/2011 | Zhou et al. |
| 2012/0094307 A1 | 4/2012 | Tajima |
| 2012/0120397 A1 | 5/2012 | Furtaw et al. |

OTHER PUBLICATIONS

International Search Report and Written Opinion dated Jul. 9, 2013 for PCT application No. PCT/US2013/03383.

Severinghaus et al., "Correction Factors for Infrared Carbon Dioxide Pressure Broadening by Nitrogen, Nitrous Oxide and Cyclopropane", Anesthesiology, vol. 22, pp. 429-432, Jan. 1, 1961.

Tang, et al., "A New Calibration Method that Compensates for the Effects of O2 and N2 on Infrared CO2 Analysers", Journal of Clinical Monitoring and Computing, vol. 20, No. 2, pp. 75-79, Jun. 8, 2006.

* cited by examiner

COLLISIONAL BROADENING COMPENSATION USING REAL OR NEAR-REAL TIME VALIDATION IN SPECTROSCOPIC ANALYZERS

CROSS-REFERENCE TO RELATED APPLICATIONS

The current application is a continuation of U.S. patent application Ser. No. 13/428,591 filed Mar. 23, 2012 and is related to co-pending and co-owned U.S. patent application Ser. No. 13/026,921 and co-pending and co-owned U.S. patent application Ser. No. 13/027,000 and to co-owned U.S. Pat. No. 7,508,521, co-owned U.S. Pat. No. 7,704,301, and co-owned U.S. Pat. No. 7,819,946. The disclosure of each of the related applications and patents is incorporated herein by reference in its entirety.

TECHNICAL FIELD

The subject matter described herein relates to compensation for the effects of collisional broadening on measurements, for example for detection and/or quantification of trace gases, made by spectroscopic analyzers.

BACKGROUND

Spectroscopic analysis generally relies on detection and quantification of emission or absorption of radiation by matter (e.g. individual molecules in analysis of gas phase compounds). The radiation is absorbed or emitted with a particular energy determined by transitions occurring to the molecules of an analyte. For example, in infrared spectroscopy, discrete energy quanta are absorbed by molecules due to excitation of vibrational or rotational transitions of the intra-molecular bonds. The collision of other molecules in a gas mixture with the emitting or absorbing molecules and the collision between the emitting or absorbing molecules themselves can perturb the energy levels of the emitting or absorbing molecules and therefore cause broadening of the emission or absorption line shape. Broadening of spectral line shapes can depend on any or all of the pressure, the temperature, and composition of the gas mixture in addition to the spectral transition and concentration of a particular target analyte. Quantitative measurement errors can occur if the spectroscopic analyzer is used to measure a target analyte in a sample gas with combination of pressure, temperature and composition of background gas that differs from the gas mixture used to calibrate the analyzer. These errors have been found to be a substantial challenge for optical measurement of important trace level impurities (e.g. less than approximately 10,000 ppm) in natural gas quality control, petrochemical production, quality control and environmental emissions control, and the like, but are not limited to those applications. The important impurities can include but are not limited to water ($H_2O$), hydrogen sulfide ($H_2S$), other sulfur compounds, other acids, carbon dioxide ($CO_2$), carbon monoxide (CO), ammonia ($NH_3$), acetylene ($C_2H_2$), other hydrocarbons, other hydro-fluoro-chloro-carbons, and combinations thereof.

One or more approaches can be applied to compensate for broadening caused by differences in pressure and temperature during quantitative target analyte analysis. For example, the pressure and/or temperature of the sample gas can be maintained sufficiently close to the calibration gas pressure and/or temperature by proper sample conditioning, including pressure regulation and temperature stabilization of the sample gas. In another example, real time measurement of pressure and temperature can be used to compensate for the collisional broadening change by applying theoretical models, including but not limited to polynomial corrections, pressure temperature matrixes, chemometrics, experimental calibrations, and the like. In another example parameters of the spectroscopic measurement (e.g. the harmonic modulation parameters) can also be adjusted in real time to compensate for line shape broadening due to changes in sample gas pressure. An example of such an approach is described in co-owned U.S. Pat. No. 7,508,521, the disclosure of which is incorporated herein by reference.

Direct absorption spectroscopy approaches can be used for measurement of target analyte concentrations exceeding approximately 10,000 ppm and background gas mixes which offer little or substantially no interfering absorption at the wavelength of the target analyte spectral line. Integration over the some or all of the line shape of the target analyte spectrum can provide a quantitative target analyte concentration, which is proportional to the area of the spectral line shape but does not depend upon the line shape itself.

However, there are currently no available approaches that provide experimental or theoretical compensation of spectral line shape changes caused by collision of the target analyte with molecules in a gas sample having different mass and structure and as a result of changing composition of the gas sample. Compensating for spectral line shape changes caused by changing background sample gas composition is critically important, especially for all harmonic spectroscopy approaches, which typically have to be used to measure target analyte concentrations below approximately 10,000 ppm and from ppb levels (e.g. approximately 1 to 5 ppb) to parts per hundred (e.g. approximately 1% to 10% or even to 75% or higher) in sample gases which include absorption by one or more compounds present at non-negligible concentrations in the background and in applications in which spectrally broadly absorbing gases are present or in which accumulation of condensates on optical surface sin the absorbing beam path is expected to occur. As an example, pipeline corrosion protection and natural gas tariff control in the United States typically require measurement of water vapor ($H_2O$) in natural gas streams within an uncertainty limit of ±4 ppm, over a range of approximately 0 ppm to 400 ppm or higher. The composition of a typical natural gas stream can change over a very wide range, with methane ($CH_4$) tending to vary within a mole fraction range of approximately 50% to 100%; carbon dioxide ($CO_2$) tending to vary within a mole fraction range of approximately 0% to 15%; and ethane ($C_2H_6$), propane ($C_3H_8$), and butane ($C_4H_{10}$) combined tending to vary in accordance with actual methane and carbon dioxide concentrations to make up 100% of the natural gas stream.

Typical industry standard moisture analyzers based on tunable diode laser spectrometers, for example a Spectra-Sensors model SS2000 (available from SpectraSensors, Inc. of Houston, Tex.) or a General Electric Aurora (available from GE Measurement & Control Solutions of Billerica, Mass.) may not be capable of providing necessary measurement accuracy over such a wide range of stream component variation due to the spectral line shape broadening caused by unknown gas sample composition. In another example, the U.S. Department of Energy (DOE) sponsored an evaluation project entitled "Development of In Situ Analysis for the Chemical Industry" that was conducted by the DOW Chemical Company and that concluded that harmonic spectroscopy tunable diode lasers are not well suited for gas analysis applications in the chemical industry due to their measurement sensitivity to gas composition changes. The report detailing the results of this study: "In-Situ Sensors for the Chemical Industry—Final Report," the Dow Chemical Company, Principle investigator: Dr. J. D. Tate, project No. DE-FC36-o21D14428, pp. 1-37, Jun. 30, 2006, is incorporated herein by reference.

SUMMARY

In one aspect of the currently disclosed subject matter, a method includes receiving or collecting validation verification data quantifying an intensity of light reaching a detector of a spectrometer from a light source of the spectrometer after the light passes through a validation gas across a known path length. The validation gas includes a known amount of an analyte compound and an undisturbed background composition that is representative of a sample gas background composition of a sample gas to be analyzed using a spectrometer. The sample gas background composition includes one or more background components other than the analyte compound. The validation verification data are compared with stored calibration data for the spectrometer to calculate a concentration adjustment factor, and the concentration adjustment factor is used to modify sample measurement data collected with the spectrometer to compensate for collisional broadening of a spectral peak of the analyte compound by the background components in the sample gas.

In interrelated aspects of the current subject matter, an apparatus can include a tangibly embodied machine-readable medium operable to or otherwise storing instructions that cause one or more machines (e.g., computers, programmable processors, etc.) to perform operations as described herein. Similarly, computer systems are also described that may include at least one processor and a memory coupled to the at least one processor. The memory may include one or more programs that cause the at least one processor to perform one or more of the operations described herein.

In optional variations, one or more of the following features can be included in a method or apparatus in any feasible combination. A method can optionally include generating the validation gas, and an apparatus can include a validation gas generation system. The generating of the validation gas (for example by a validation gas generation system) can optionally include treating a volume of the sample gas to remove or otherwise substantially reduce a concentration of the analyte compound, and adding a known mass of the analyte compound to the treated sample gas volume. The treating of the volume of the sample gas can optionally include directing the volume of the sample gas through a gas processor, which can optionally include at least one of a scrubber, a purifier, a chemical converter, a chemical separator, a distillation column, a separation column, a dryer, and the like. The known mass of the analyte compound can optionally be added (for example by a validation gas generation system) by a process comprising one or more of adding a measured volume of the analyte compound as a gas, liquid, or solid to the volume of the treated sample gas; flowing the volume of the treated sample gas as a treated sample gas stream past an analyte compound source that emits the analyte compound into the treated sample gas stream at a known and controlled mass and/or volume flow rate; and adding, at a known flow rate, a gas mixture containing the analyte compound at a known concentration to the treated sample gas stream.

The calculation of the concentration adjustment factor can optionally include determining one or more of a difference, a ratio, a mean square error (mse), a coefficient of determination ($R^2$), a cross correlation function, a cross correlation integral, and a regression coefficient in one or more of a light intensity domain and a wavelength domain for one or more parts or an entirety of the validation verification data and the calibration data. The determining can optionally include using one or more mathematical methods of subtracting, dividing, cross correlation, convolution, curve fitting, regression, and optimization. The calculation of the concentration adjustment factor can optionally include application of a chemometrics-based method.

In further optional variations, an apparatus can optionally include a light source, which can include, but is not limited to one or more of a tunable diode laser, a tunable semiconductor laser, a quantum cascade laser, a vertical cavity surface emitting laser (VCSEL), a horizontal cavity surface emitting laser (HCSEL), a distributed feedback laser, a light emitting diode (LED), a super-luminescent diode, an amplified spontaneous emission (ASE) source, a gas discharge laser, a liquid laser, a solid state laser, a fiber laser, a color center laser, an incandescent lamp, a discharge lamp, and a thermal emitter. An apparatus can also optionally include a detector, which can include, but is not limited to one or more of an indium gallium arsenide (InGaAs) detector, an indium arsenide (InAs) detector, an indium phosphide (InP) detector, a silicon (Si) detector, a silicon germanium (SiGe) detector, a germanium (Ge) detector, a mercury cadmium telluride detector (HgCdTe or MCT), a lead sulfide (PbS) detector, a lead selenide (PbSe) detector, a thermopile detector, a multi-element array detector, a single element detector, and a photo-multiplier.

Implementations of the current subject matter can provide one or more advantages. For example, the flow configuration used in validating a spectroscopic measurement can impact the accuracy and repeatability of the validation and thus its applicability to collisional broadening compensation. Approaches consistent with the current subject matter enable the use of a validation stream whose composition, with the exception of the concentration of the one or more analyte compounds, closely mimics that of the sample gas in which the one or more analyte compounds are detected and/or quantified. Application of a concentration adjustment factor as described herein can establish calibration fidelity of a spectroscopic analyzer, even with a changing background composition of the gas being sampled. This capability can constitute a significant advance, for example with harmonic spectroscopy, which suffers from collisional broadening causing reading offsets that are generally difficult or even impossible to accurately model.

The details of one or more variations of the subject matter described herein are set forth in the accompanying drawings and the description below. Other features and advantages of the subject matter described herein will be apparent from the description and drawings, and from the claims. It should be noted that the current subject matter contemplates both a flowing sample gas stream and a static sample gas from which a sample gas volume can be withdrawn. The term "sample gas volume" or "gas volume" as used herein therefore refers to either a flowing volume or a static, batch volume of gas.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

To address the aforementioned and other potential issues with analytical validation of spectroscopic measurements, implementations of the current subject matter can provide a trace gas generator that adds a known and temporally consistent and stable amount of a trace analyte to a gas stream to facilitate the use of that gas stream as a validation stream for use in validation of a spectrometer and compensation for collisional broadening effects that can impact the analysis. Approaches consistent with implementations of the current subject matter can be advantageous for in-the-field preparation of a standard validation gas for use in conjunction with systems that detect and/or quantify a concentration of one or more trace analytes in a gas mixture that includes a complex and/or varying background of other compounds whose spectral absorbance characteristics may or may not overlap with those of the trace analyte(s). Such approaches can also be advantageous for measurement of one or more trace analytes in a toxic, environmentally incompatible, or corrosive background, such as for example vinyl-chloride monomers (VCM), chlorine ($Cl_2$), ammonia ($NH_3$), hydrogen chloride (HCl), hydrogen fluoride (HF), hydrogen sulfide ($H_2S$), hydrogen arsenide ($AsH_3$), hydrogen phosphide ($PH_3$), hydrogen cyanide (HCN), and the like, for which previously available approaches may have required substitution of a non-toxic gas, such as for example nitrogen ($N_2$), for the calibration of the optical trace gas analyzer. Approaches consistent with implementations of the current subject matter can also be advantageous for measurement of one or more trace analytes in a gas mixture containing toxic, environmentally incompatible, or corrosive compounds that have to be eliminated or substituted during the calibration.

Gas sampled from a gas source can include one or more analyte compounds. Detection and/or quantification of the concentration of such analyte compounds can be performed by spectroscopic analysis. To compensate for the effects of collisional broadening on the results of the spectroscopic analysis, the current subject matter makes use of a validation stream that resembles the sample gas as closely as is possible. The validation stream can be prepared by first selectively removing or at least substantially reducing the concentration of the analyte or analytes in the sample gas from the gas source and then adding the analyte or analytes to the neat (free of the analyte or analytes) sample gas at a well controlled and accurately known mass and/or volume (note: perm tube vs. premixed bottle) delivery rate to produce a consistent, controlled, and well known concentration of the analyte or analytes in the validation stream. A test spectrum collected using this validation stream can be compared to a previously stored reference spectrum collected using the same analytical system during a calibration process. Based on this comparison, a concentration adjustment factor can be determined to account for differences between a first background condition, including for example chemical composition, pressure and temperature, etc., of the validation stream and a second background condition of a calibration gas used to prepare the stored reference spectrum. Alternatively, a test spectrum collected using the sample stream can be compared to the test spectrum collected using the validation stream instead of the previously stored reference spectrum to directly generate a more accurate concentration reading.

Analyte compounds with which implementations of the current subject matter can be used include, but are not limited to, hydrogen sulfide ($H_2S$); hydrogen chloride (HCl); water vapor ($H_2O$); hydrogen fluoride (HF); hydrogen cyanide (HCN); hydrogen bromide (HBr); ammonia ($NH_3$); arsine ($AsH_3$); phosphine ($PH_3$); oxygen ($O_2$); carbon monoxide (CO); carbon dioxide ($CO_2$); hydrocarbons, including but not limited to methane ($CH_4$), ethane ($C_2H_6$), ethene ($C_2H_4$), acetylene ($C_2H_2$), etc.; and the like.

Figure 1:
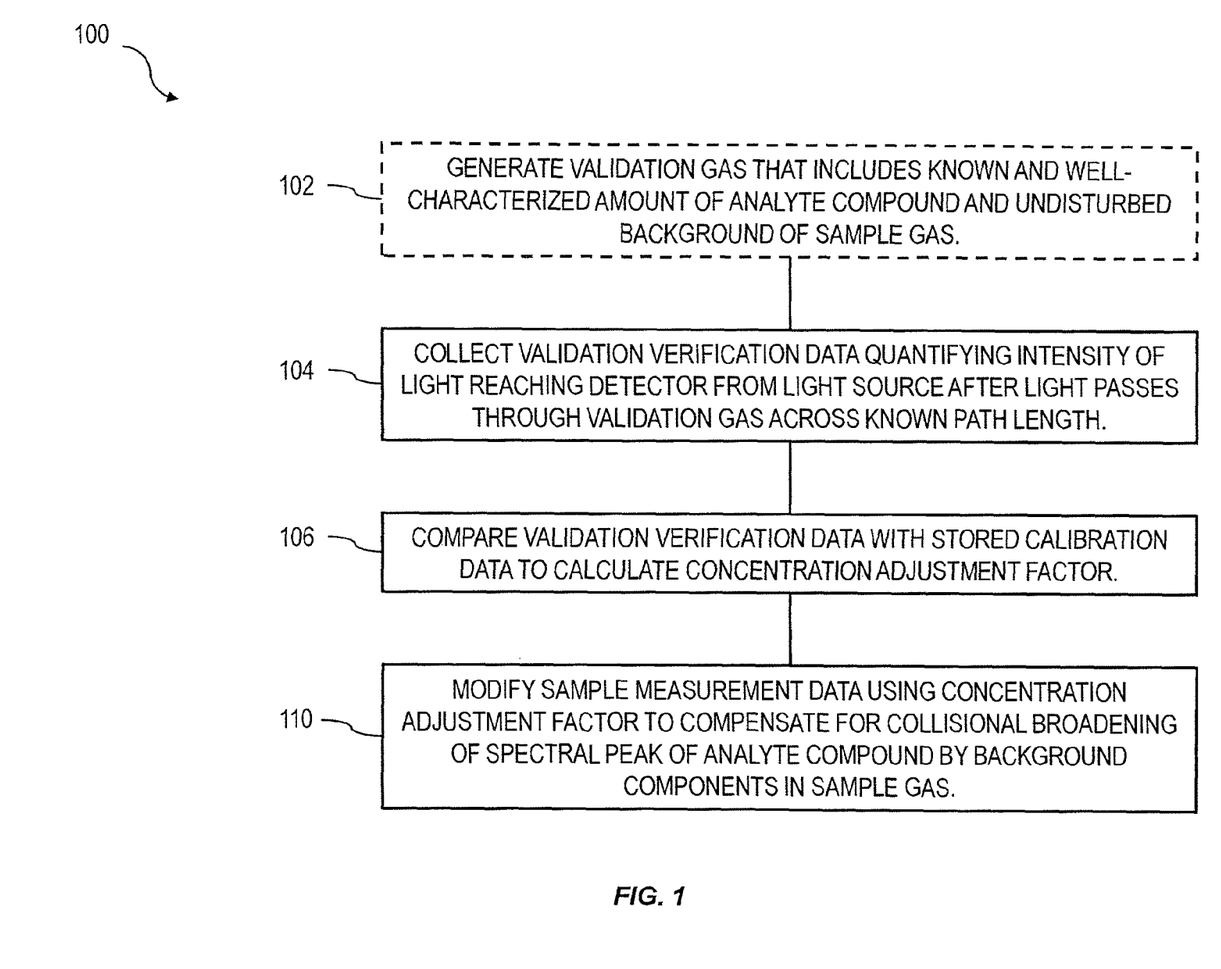
FIG. 1 is a process flow diagram illustrating aspects of a method having one or more features consistent with implementations of the current subject matter.

The flow chart 100 of FIG. 1 illustrates features of a method consistent with at least some implementations of the current subject matter. At 102, a validation gas is generated to contain one or more analyte compounds in an amount or concentration that is known or at least well-characterized. As used herein, the term "known" is intended to refer to a concentration, amount, or the like that is known to the extent possible in light of inherent errors in measurement of an amount or concentration of a validation gas. In some situations, it is acknowledged and one of ordinary skill in the art would readily understand that it may not be feasible to "know" the amount or concentration of the one or more analytes in a validation gas to a complete certainty. In such cases, such an amount or concentration can in some examples be considered to be "well-characterized" if measured to the accuracy of an available instrument or instruments or otherwise produced in a reasonably well-controlled and reasonably reproducible manner. When the term "known" is used herein in reference to a concentration of an analyte, it should be readily understood that the foregoing explanation applies and that descriptions herein of known concentrations or amounts are assumed to refer to such values that are known and/or well-characterized within a reasonable margin of error.

In an implementation, a validation gas can be generated by first treating a volume of a sample gas to remove or otherwise substantially reduce a concentration of an analyte compound in the sample gas, for example by directing the sample gas through a gas processor, which can optionally include but is not limited to a scrubber, a purifier, a dryer, a chemical treatment or conversion process, or the like. To generate the known concentration of the analyte compound in the treated sample gas volume, after treating the sample gas volume by the gas processor, an analyte compound can added to the treated sample gas stream at a known (or at least well-characterized) and controlled mass and/or volume flow rate. A known mass of the analyte compound can be added using one or more processes, including but not limited to adding a measured volume of the analyte compound as a gas, liquid, or solid to the volume of the treated sample gas; flowing the volume of the treated sample gas as a treated sample gas stream past an analyte compound source that emits the analyte compound into the treated sample gas stream at a known and controlled mass and/or volume flow rate; and adding, at a known flow rate, a gas mixture containing the analyte compound at a known concentration to the treated sample gas stream.

At 104, validation verification data, for example a test spectrum, are received or collected for the validation gas, for example at a programmable processor that can be local to the spectrometer or remotely connected via a wired or wireless network or other communication link. The receiving of the validation verification data can occur synchronously with its generation by the spectrometer or asynchronously (e.g. with a time delay for transmission or in discrete packets of data). The validation verification data quantify a first intensity of light reaching a detector from a light source after the light passes through the validation stream across a first known path length. The validation verification data are compared at 106 with stored calibration data, for example a previously stored reference spectrum collected with the same analyzer system using a reference gas of a known concentration, to calculate a concentration adjustment factor. At 110, the concentration adjustment factor is used to modify sample measurement data quantifying a second intensity of light reaching the detector from the light source after the light passes through a sample stream or volume of sample gas across a second known path length that can include all or part of the first known path length. The modifying of the sample measurement data can provide a compensation for collisional broadening of spectral peaks of the one or more analyte compounds in the sample gas. This compensation can be used to provide a more accurate measurement and/or to validate a measurement of a spectral analyzer relative to a previous calibration state.

The concentration adjustment factor can be calculated as one or more of the difference, the ratio, the mean square error (mse), the coefficient of determination ($R^2$), the cross correlation function or integral, the regression coefficients in one or more of the light intensity domain and the wavelength domain, and the like for one or more parts or the entirety of the validation verification data and the calibration data using one or more mathematical methods of subtracting, dividing, cross correlation, convolution, curve fitting, regression, optimization, and the like. The concentration adjustment factor can be used to modify the sample measurement data before or after comparing the sample measurement data with the calibration data. The modification of the sample measurement data using the concentration adjustment factor can utilize one or more mathematic methods of subtracting, dividing, cross correlation, convolution, curve fitting, regression and optimization. Alternatively, the sample measurement data can be compared to the validation verification data instead of the calibration data to directly generate the more accurate concentration reading. The comparison of the sample measurement data and the validation verification data can utilize one or more mathematical methods of subtracting, dividing, cross correlation, convolution, curve fitting, regression, optimization, and the like to generate the ratio between the sample measurement data and the validation verification data.

Figure 2:
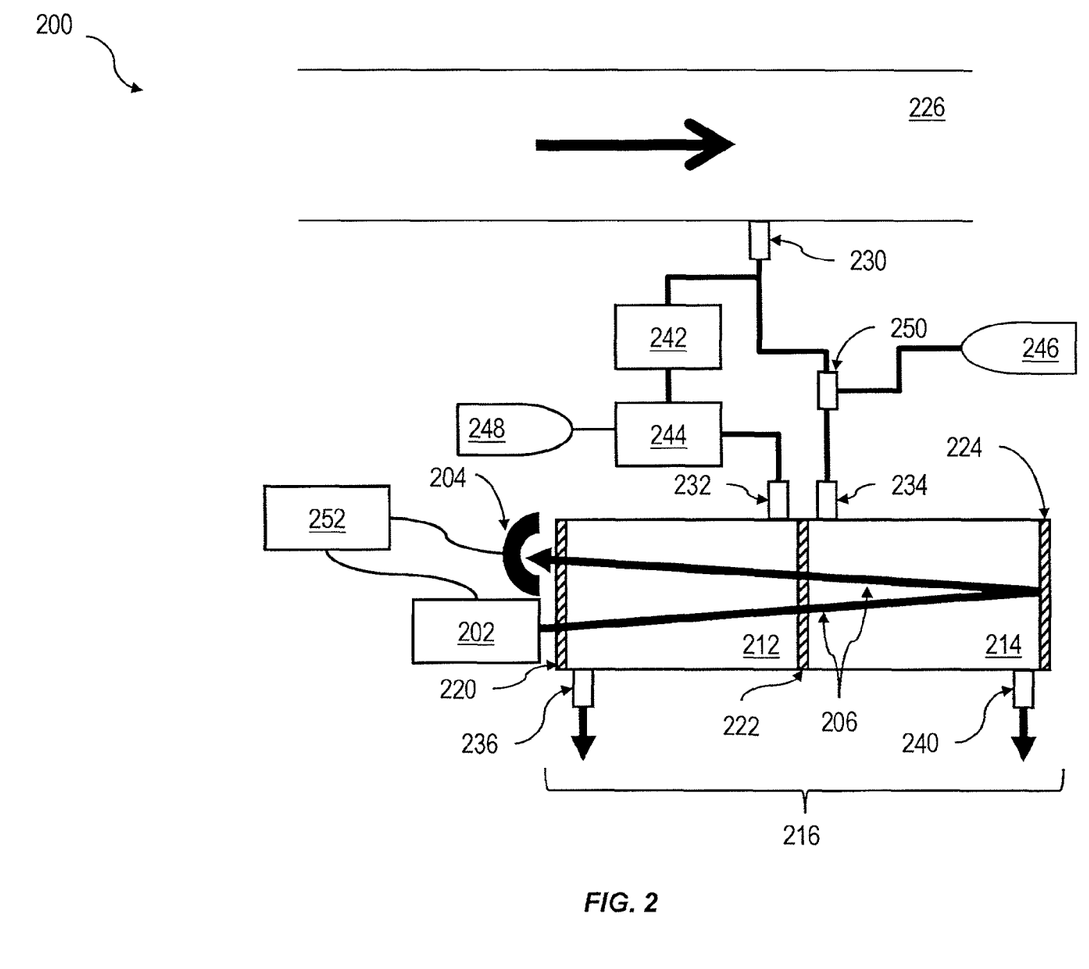
FIG. 2 is a diagram illustrating aspects of a system showing features consistent with implementations of the current subject matter.

FIG. 2 shows an example of a system 200 having features consistent with one or more implementations of the current subject matter. A light source 202 provides a continuous or pulsed light that is directed to a detector 204 via a path length 206. The path length 206 can traverse one or more gas volumes. In the example system 200 shown in FIG. 2, the path length 206 twice traverses each of a first volume 212 and a second volume 214, which are contained within a single optical cell 216 that includes a first window or other at least partially radiation transmissive surface 220, a second window or other radiation transmissive surface 222, and a mirror or other at least partially radiation reflective surface 224 that at least partially define the first volume 212 and the second volume 214. Sample gas can, in some implementations, be obtained from a gas source, which in the example of FIG. 2 is a pipeline 226, for delivery to the first volume 212 and the second volume, for example via a sample extraction port or valve 230 that receives the sample gas from the source and a first inlet port 232 delivering gas to the first volume 212 and a second inlet port 234 delivering gas to the second volume 214. Gas in the first volume 212 can exit the first volume 212 via a first outlet valve or port 236 and gas in the second volume 214 can exit the second volume 212 via a second outlet valve or port 240

Gas passing to the first volume 212 can be directed first through a gas processor 242 that removes or at least reduces a concentration of the analyte compound in the gas flowing to the first volume 212 as a first process in creating a validation stream. The gas processor 242 can advantageously not substantially affect the concentration of at least one background compound in the validation stream. The gas processor 242 can optionally be a scrubber, a purifier, a dryer, a chemical conversion unit, or the like that reduces a concentration of the analyte compound in the validation stream, advantageously to an at least approximately negligible level, for example by chemically or physically removing the analyte compound from the gas phase to another phase (e.g. solid, adsorbed, absorbed, liquid, dissolved, etc.) or by chemically converting the analyte compound to another chemical species whose spectral characteristics differ sufficiently from those of the analyte compound so as to not interfere with measurements at a narrow line width spectral region focused on an absorption or emission characteristic of the analyte compound.

The validation stream can pass from the gas processor 242 to an analyte generator 244 that adds the analyte compound to the validation stream. In some variations, the analyte generator 244 can be one or more diffusion-type gas generators, such as for example one or more osmotic membrane generators or permeation tubes (an illustrative example of which is the G-Cal product line available from VICI Metronics of Poulsbo, Wash.). Alternatively, the analyte generator 244 can be a mixer that blends premixed analyte in one or more carrier gases from a compressed gas cylinder 248 with the neat sample stream flowing out of the gas processor 242.

The first volume 212 and the second volume 214 can in some implementations be configured as a sample measurement cell and a validation cell such as those illustrated and described in co-pending and co-owned application for U.S. patent Ser. No. 13/026,921 and Ser. No. 13/027,000, the disclosures of which are incorporated herein by reference. Other configurations are within the scope of the current subject matter. For example, either or both of the first volume 212 and the second volume 214 can be free gas space, for example part or all of the exhaust stack of a combustion installation, chemical processing plant, etc.

As shown in FIG. 2, each of the first volume 212 and the second volume 214 can be configured as separate optical cells, one for containing a volume of the validation stream, and the other for containing either an untreated volume of the sample gas or a "zero gas" having at least one of known and negligible first light absorbance characteristics that overlap second light absorbance characteristics of the analyte compound within a wavelength range of the light provided by the light source 202. The zero gas can in some implementations be a gas provided from a compressed gas cylinder 246 connected to a supply line to the second inlet port 234 via a connector port or valve 250. The zero gas can optionally include one or more of a noble gas, nitrogen gas, oxygen gas, air, hydrogen gas, a homo-nuclear diatomic gas, at least a partial vacuum, a hydrocarbon gas, a fluoro-carbon gas, a hydro-fluoro-carbon gas, a chloro-carbon gas, a chloro-fluoro-carbon gas, a hydro-chloro-carbon gas, a hydro-fluoro-chloro-carbon gas, carbon monoxide gas, carbon dioxide gas, some other gas including known concentrations of one or more compounds with known, or optionally at least well characterized, spectroscopic responses at one or more wavelengths provided by the light source 202, or the like. The zero gas can optionally be passed through a scrubber or chemical converter to remove or reduce a concentration of the trace analyte therein before directing the zero gas into the path of the light.

A controller 252, which can include one or more programmable processors or the like, can communicate with one or more of the light source 202 and the detector 204 for controlling the emission of the light 206 and receiving signals generated by the detector 204 that are representative of the intensity of light impinging on the detector 204 as a function of wavelength. In various implementations, the controller 252 can be a single unit that performs both of controlling the light source 202 and receiving signals from the detector 204, or it can be more than one unit across which these functions are divided. Communications between the controller 252 or controllers and the light source 202 and detector 204 can be over wired communications links, wireless communications links, or any combination thereof.

One or both of the first volume 212 and the second volume 214 can be maintained at a stable temperature and pressure. Alternatively, one or both of the first volume 212 and the second volume 214 can include one or more temperature and/or pressure sensors to determine a current temperature and pressure within that volume for use in one or more calculations to compensate for temperature and/or pressure changes relative to a validation or calibration condition of the spectroscopic instrument.

The system 200 can be operated to perform a collisional broadening compensation measurement as discussed above by running the validation gas through the first volume 212 and the zero gas through the second volume 214. To perform a measurement of the analyte concentration in the gas from the gas source, the sample gas can be directed into the second volume 214. During this process, the validation gas can continue to be provided to the first volume 212. The light intensity arriving at the detector 204 from the light source 202 after traversing the path length can be corrected mathematically to account for absorption by the analyte compound present in the validation gas in the first volume 212.

Figure 3:
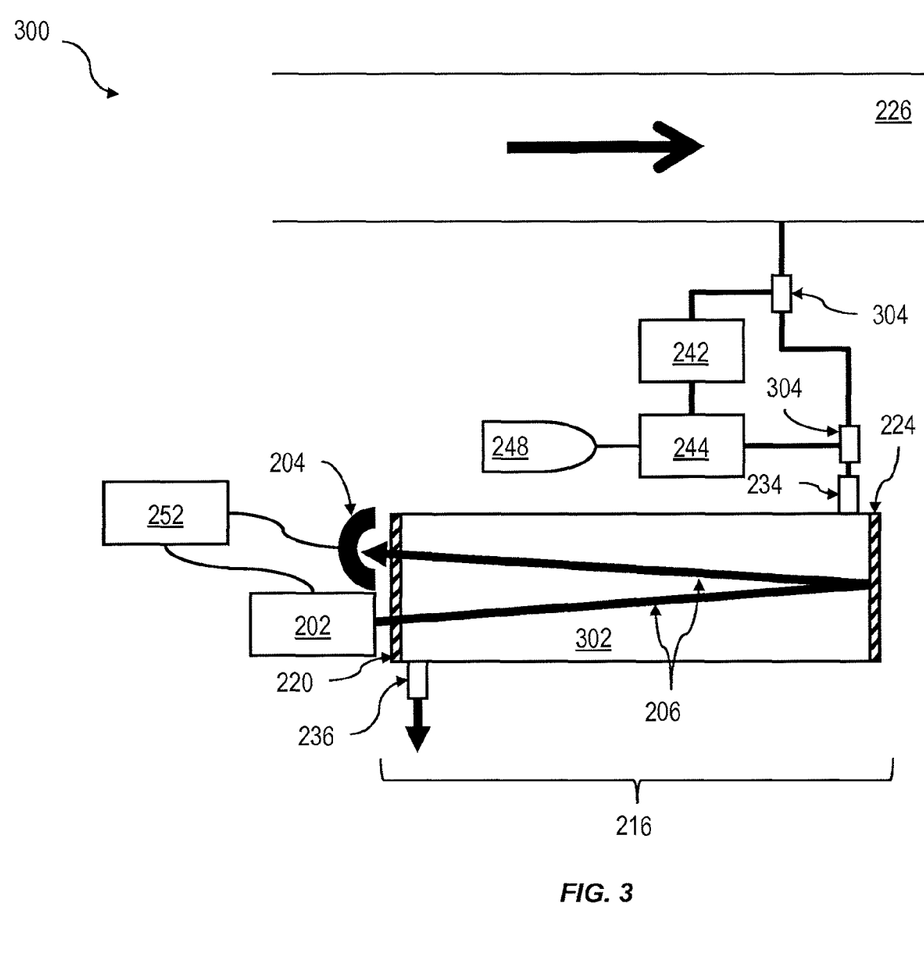
FIG. 3 is a diagram illustrating aspects of another system showing features consistent with implementations of the current subject matter.

In another implementation, which is illustrated in FIG. 3, a system includes a single volume 302 within an optical cell 216. One or more flow switching valves or comparable devices 304 can be included on a sample gas supply line from a gas source, which can be a pipeline 226 as shown in FIG. 3, some other source of sample gas, or the like. The flow switching valves or comparable devices 304 can be switched to direct gas from the gas source to flow through a gas processor 242 and an analyte generator 244 to generate a validation gas as discussed above. The validation gas is delivered to the single volume 302 via the inlet port or valve 234. The system 300 can be operated to perform a collisional broadening compensation measurement as discussed above by running this validation gas through the single volume 302. To perform a measurement of the analyte concentration in the gas from the gas source, the flow switching valves or comparable devices 304 can be switched to direct gas to the single volume 302 via the inlet port or valve 234 without passing through the gas processor 242 and the analyte generator 244.

The controller 252, or alternatively one or more other processors that are either collocated with the other components or in wireless, wired, etc. communication therewith, can perform the processing functions discussed above in reference to the method illustrated in FIG. 1.

Figure 4:
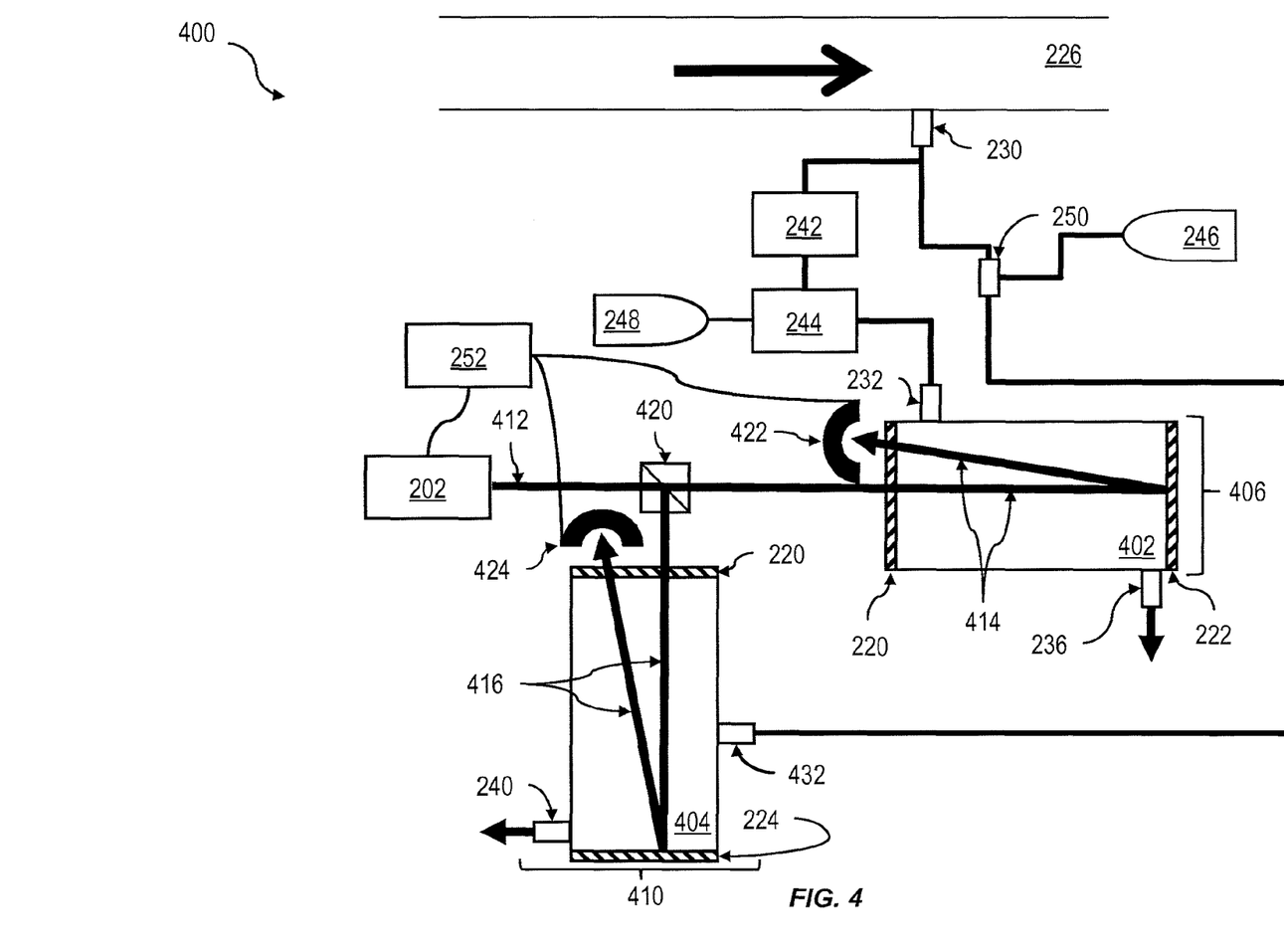
FIG. 4 is a diagram illustrating aspects of yet another system showing features consistent with implementations of the current subject matter.

In yet another implementation, which is illustrated in FIG. 4, a system 400 includes a first volume 402 and a second volume 404 included within two separate optical cells 406 and 410, respectively. The initial laser beam or series of laser pulses 412 from the laser source 202 can be split into a first split beam 414 and a second split beam 416 via a beam splitting, demultiplexing, etc. device 420, which can include free space or fiber based beam splitters, gratings, fiber splitters, or other partial radiation transmissive and/or anti-reflective or reflective surfaces, which can include, but are not limited to oxides, such as for example silicon dioxide ($SiO_2$), titanium dioxide ($TiO_2$), aluminum oxide ($Al_2O_3$), hafnium oxide ($HfO_2$), zirconium oxide ($ZrO_2$), scandium oxide ($Sc_2O_3$), niobium oxide ($NbO_2$), and tantalum oxide ($Ta_2O_5$); fluorides, such as for example magnesium fluoride ($MgF_2$), lanthanum fluoride ($LaF_3$), and aluminum fluoride ($AlF_3$); etc.; and/or combinations thereof; metallic materials including but not limited to gold (Au), silver (Ag), copper (Cu), steel, aluminum (Al), and the like; one or more layers of transparent dielectric optical materials (e.g. oxides, fluorides, etc.); and/or a combination of metallic and dielectric optical materials or the like. The first split beam 414 traverses the first volume 402 one or more times before reaching a first detector 422. The second split beam 416 transverses the second volume 404 one or more times before reaching a second detector 424.

A controller 252 controls the light source 202 and receives signals from the detectors 422 and 424. The system 400 can be operated to perform a collisional broadening compensation measurement as discussed above by running the validation gas through the first volume 402 and the untreated sample gas through the second volume 404 at either the same time or at different times.

In an alternative implementation of the system shown in FIG. 4, the two split beams 414 and 416 can be combined into a single beam, after having exited from the first volume 402 and the second volume 404 respectively, by one or more beam multiplexing devices, which can include one or more of gratings, fiber combiners or partial radiation transmissive and/or anti-reflective or reflective surfaces. In this implementation, the multiplexed single beam can be detected by a single detector, which provides signals to the controller.

Both sample measurement and the validation verification measurements as described herein can optionally be used in conjunction with a differential absorption approach, including but not limited to those described in co-owned U.S. Pat. No. 7,704,301 and co-owned U.S. Pat. No. 7,819,946. When a differential absorption method is used, an analytical system, for example one including one or more features shown in FIG. 2 through FIG. 4 or otherwise within the scope of the current subject matter, can be modified to include a gas processor similar to gas processor 242 and one or more flow switching valves or comparable devices similar to a device 304.

In various implementations of the current subject matter, the validation stream can be used in conjunction with a flow-through validation cell such as is described in co-pending and co-owned U.S. patent application Ser. No. 13/026,921 and co-pending and co-owned U.S. patent application No. 13/027,000. The light source 202 can include, for example, one or more of a tunable diode laser, a tunable semiconductor laser, a quantum cascade laser, a vertical cavity surface emitting laser (VCSEL), a horizontal cavity surface emitting laser (HCSEL), a distributed feedback laser, a light emitting diode (LED), a super-luminescent diode, an amplified spontaneous emission (ASE) source, a gas discharge laser, a liquid laser, a solid state laser, a fiber laser, a color center laser, an incandescent lamp, a discharge lamp, a thermal emitter, and the like. The detector 206 can include, for example, one or more of an indium gallium arsenide (InGaAs) detector, an indium arsenide (InAs) detector, an indium phosphide (InP) detector, a silicon (Si) detector, a silicon germanium (SiGe) detector, a germanium (Ge) detector, a mercury cadmium telluride detector (HgCdTe or MCT), a lead sulfide (PbS) detector, a lead selenide (PbSe) detector, a thermopile detector, a multi-element array detector, a single element detector, a photomultiplier, and the like.

Optical configurations consistent with one or more implementations of the current subject matter can optionally include at least one optical feature for transmitting and/or reflecting the beam of light 206 between the light source 202 and the detector 204. Such optical components can advantageously have a low absorbance of light at the wavelength or range of wavelengths at which the light source 202 emits the light. In other words, a reflective optical component would advantageously reflect more than 50% of the incident light at the wavelength or in the range of wavelengths, in a single reflection, an optical light guide would advantageously transmit more than 1% of the incident light, and a window would advantageously be anti-reflection coated and transmit more than 90% of the incident light at the wavelength or in the range of wavelengths.

Implementations of the approach described herein can be applicable to any laser absorption spectrometer that includes a tunable laser source, including but not limited to direct absorption spectrometers, harmonic absorption spectrometers, differential absorption spectrometers, etc. For a direct absorption spectrometer, the measurement of trace analyte concentrations can be performed without using a harmonic conversion or demodulation of the signal obtained from the detector. However, periodic or continuous recalibration of the laser light source, detector, etc. can be performed using a calibration circuit, etc. that makes use of a harmonic signal obtained from the detector signal.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like. A computer remote from an analyzer can be linked to the analyzer over a wired or wireless network to enable data exchange between the analyzer and the remote computer (e.g. receiving data at the remote computer from the analyzer and transmitting information such as calibration data, operating parameters, software upgrades or updates, and the like) as well as remote control, diagnostics, etc. of the analyzer.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claim.

What is claimed is:

1. A method comprising:

calculating a first concentration adjustment factor, the first concentration adjustment factor accounting for first differences between a first validation gas background condition of a first validation gas and a calibration gas background condition of a calibration gas used to prepare a stored reference spectrum, the first validation gas being representative of a first background concentration of at least one background component in a first sample gas, the first sample gas comprising an analyte compound at a first unknown concentration in addition to the at least one background component at approximately the first background concentration, the calculating of the first concentration adjustment factor comprising comparing first validation verification data with the stored reference spectrum, the first validation verification data quantifying a first intensity of light reaching a detector of a spectrometer from a light source of the spectrometer after the light passes through the first validation gas over a wavelength range of the light provided by the light source;

modifying, using the first concentration adjustment factor, first sample measurement data collected with the spectrometer to compensate for collisional broadening of a spectral peak of the analyte compound in the first sample gas;

calculating a second concentration adjustment factor, the second concentration adjustment factor accounting for second differences between a second validation gas background condition of a second validation gas and the calibration gas background condition, the second validation gas differing from the first validation gas and being representative of a second background concentration of the at least one background component in a second sample gas, the second sample gas comprising the analyte compound at a second unknown concentration in addition to the at least one background component at approximately the second background concentration, the calculating of the second concentration adjustment factor comprising comparing second validation verification data with the stored reference spectrum, the second validation verification data quantifying a second intensity of light reaching the detector of the spectrometer from the light source of the spectrometer after the light passes through the second validation gas over the wavelength range of the light provided by the light source; and modifying, using the second concentration adjustment factor, second sample measurement data collected with the spectrometer to compensate for collisional broadening of the spectral peak of the analyte compound in the second sample gas.

2. A method as in claim 1, further comprising generating the first validation gas and the second validation gas.

3. A method as in claim 2, wherein the generating of the first validation gas comprises treating a first volume of the first sample gas to remove or otherwise substantially reduce the first unknown concentration of the analyte compound, and adding a known mass of the analyte compound to the treated first volume of the first sample gas, and wherein the generating of the second validation gas comprises treating a second volume of the first sample gas to remove or otherwise substantially reduce the second unknown concentration of the analyte compound, and adding the known mass of the analyte compound to the treated second volume of the second sample gas.

4. A method as in claim 3, wherein the treating of the first volume of the first sample gas comprises directing the first volume of the first sample gas through a gas processor, and wherein the treating of the second volume of the second sample gas comprises directing the second volume of second first sample gas through the gas processor.

5. A method as in claim 3, wherein the known mass of the analyte compound is added by a process comprising one or more of adding a measured volume of the analyte compound as a gas, liquid, or solid to the first volume of the treated first sample gas; flowing the volume of the treated sample gas as a first treated sample gas stream past an analyte compound source that emits the analyte compound into the treated first sample gas stream at a known and controlled mass and/or volume flow rate; and adding, at a known flow rate, a gas mixture containing the analyte compound at a known concentration to the treated first sample gas stream.

6. A method as in claim 1, wherein the calculating of the first concentration adjustment factor and the calculating of the second concentration adjustment factor comprise determining one or more of a difference, a ratio, a mean square error (mse), a coefficient of determination ($R^2$), a cross correlation function, a cross correlation integral, and a regression coefficient in one or more of a light intensity domain and a wavelength domain for one or more parts or an entirety of the validation verification data and the calibration data.

7. A method as in claim 6, wherein the determining comprises using one or more mathematical methods of subtracting, dividing, cross correlation, convolution, curve fitting, regression, and optimization.

8. A method as in claim 1, wherein the calculating of the first concentration adjustment factor and the calculating of the second concentration adjustment factor comprise application of a chemometrics-based method.

9. A method as in claim 1, wherein the second validation gas differs from the first validation gas in at least one of pressure and temperature.

10. A method as in claim 1, wherein the first background concentration differs from the second background concentration.

11. An apparatus comprising:

a non-transitory machine readable medium storing instructions that, when executed by at least one programmable processor, cause the at least one programmable processor to perform operations comprising:

calculating a first concentration adjustment factor, the first concentration adjustment factor accounting for first differences between a first validation gas background condition of a first validation gas and a calibration gas background condition of a calibration gas used to prepare a stored reference spectrum, the first validation gas being representative of a first background concentration of at least one background component in a first sample gas, the first sample gas comprising an analyte compound at a first unknown concentration in addition to the at least one background component at approximately the first background concentration, the calculating of the first concentration adjustment factor comprising comparing first validation verification data with the stored reference spectrum, the first validation verification data quantifying a first intensity of light reaching a detector of a spectrometer from a light source of the spectrometer after the light passes through the first validation over a wavelength range of the light provided by the light source;

modifying, using the first concentration adjustment factor, first sample measurement data collected with the spectrometer to compensate for collisional broadening of a spectral peak of the analyte compound in the first sample gas;

calculating a second concentration adjustment factor, the second concentration adjustment factor accounting for second differences between a second validation gas background condition of a second validation gas and the calibration gas background condition, the second validation gas differing from the first validation gas and being representative of a second background concentration of the at least one background component in a second sample gas, the second sample gas comprising the analyte compound at a second unknown concentration in addition to the at least one background component at approximately the second background concentration, the calculating of the second concentration adjustment factor comprising comparing second validation verification data with the stored reference spectrum, the second validation verification data quantifying a second intensity of light reaching the detector of the spectrometer from the light source of the spectrometer after the light passes through the second validation gas over the wavelength range of the light provided by the light source; and modifying, using the second concentration adjustment factor, second sample measurement data collected with the spectrometer to compensate for collisional broadening of the spectral peak of the analyte compound in the second sample gas.

12. An apparatus as in claim 11, further comprising a validation gas generation system that generates the first validation gas and the second validation gas.

13. An apparatus as in claim 12, wherein the validation gas generation system treats a volume of the first and second sample gas to remove or otherwise substantially reduce the first unknown concentration and the second unknown concentration of the analyte compound, and adds a known mass of the analyte compound to the treated first volume and the first sample gas and the treated second volume of the second sample gas.

14. An apparatus as in claim 13, wherein the validation gas generation system comprises a gas processor through which the first volume of the first sample gas and the second volume of the second sample gas is directed.

15. An apparatus as in claim 14, wherein the gas processor comprises at least one of a scrubber, a purifier, a chemical converter, a chemical separator, a distillation column, a separation column, and a dryer.

16. An apparatus as in claim 13, wherein the validation gas generation system adds the known mass of the analyte compound by a process comprising one or more of adding a measured volume of the analyte compound as a gas, liquid, or solid to the first volume of the treated first sample gas; flowing the volume of the treated sample gas as a first treated sample gas stream past an analyte compound source that emits the analyte compound into the treated first sample gas stream at a known and controlled mass and/or volume flow rate; and adding, at a known flow rate, a gas mixture containing the analyte compound at a known concentration to the treated first sample gas stream.

17. An apparatus as in claim 11, wherein the calculating of the first concentration adjustment factor and the calculating of the second concentration adjustment factor comprise determining one or more of a difference, a ratio, a mean square error (mse), a coefficient of determination ($R^2$), a cross correlation function, a cross correlation integral, and a regression coefficient in one or more of a light intensity domain and a wavelength domain for one or more parts or an entirety of the validation verification data and the calibration data.

18. An apparatus as in claim 17, wherein the determining comprises using one or more mathematical methods of subtracting, dividing, cross correlation, convolution, curve fitting, regression, and optimization.

19. An apparatus as in claim 11, wherein the calculating of the first concentration adjustment factor and the calculating of the second concentration adjustment factor comprises application of a chemometrics-based method.

20. A system comprising:
a light source to emit light over a wavelength range; and
a detector positioned a known path length from the light source to detect light emitted from the light source;
wherein the spectrometer performs operations comprising:
calculating a first concentration adjustment factor, the first concentration adjustment factor accounting for first differences between a first validation gas background condition of a first validation gas and a calibration gas background condition of a calibration gas used to prepare a stored reference spectrum, the first validation gas being representative of a first background concentration of at least one background component in a first sample gas, the first sample gas comprising an analyte compound at a first unknown concentration in addition to the at least one background component at approximately the first background concentration, the calculating of the first concentration adjustment factor comprising comparing first validation verification data with the stored reference spectrum, the first validation verification data quantifying a first intensity of light reaching the detector from the light source after the light passes through the first validation gas over the wavelength range;
modifying, using the first concentration adjustment factor, first sample measurement data collected with the spectrometer to compensate for collisional broadening of a spectral peak of the analyte compound in the first sample gas;
calculating a second concentration adjustment factor, the second concentration adjustment factor accounting for second differences between a second validation gas background condition of a second validation gas and the calibration gas background condition, the second validation gas being representative of a second background concentration of the at least one background component in a second sample gas, the second sample gas comprising the analyte compound at a second unknown concentration in addition to the at least one background component at approximately the second background concentration, the calculating of the second concentration adjustment factor comprising comparing second validation verification data with the stored reference spectrum, the second validation verification data quantifying a second intensity of light reaching the detector from the light source after the light passes through the second validation gas over the wavelength range; and
modifying, using the second concentration adjustment factor, second sample measurement data collected with the spectrometer to compensate for collisional broadening of the spectral peak of the analyte compound in the second sample gas.

\* \* \* \* \*